United States Patent
Janssen (10) Patent No.: US 11,116,157 B2
(45) Date of Patent: Sep. 14, 2021

(54) **METHOD OF PROPAGATING A *CANNABIS* CUTTING**

(71) Applicant: ROCKWOOL International A/S, Hedehusene (DK)

(72) Inventor: Frank Janssen, Hedehusene (DK)

(73) Assignee: ROCKWOOL INTERNATIONAL A/S, Hedehusene (DK)

(*) Notice: Subject to any disclaimer, the term of this patent is extended or adjusted under 35 U.S.C. 154(b) by 0 days.

(21) Appl. No.: 16/730,287

(22) Filed: Dec. 30, 2019

(65) Prior Publication Data
US 2021/0195860 A1 Jul. 1, 2021

(51) Int. Cl.
*A01H 4/00* (2006.01)
*A01H 6/28* (2018.01)

(52) U.S. Cl.
CPC ............. *A01H 4/005* (2013.01); *A01H 4/008* (2013.01); *A01H 6/28* (2018.05)

(58) Field of Classification Search
CPC .......... A01H 4/005; A01H 4/008; A01H 6/28; A01G 24/18; A01G 24/00; C12N 5/0068
USPC ....................................................... 435/420
See application file for complete search history.

(56) References Cited

U.S. PATENT DOCUMENTS

| | | | |
|---|---|---|---|
| 9,609,813 B2 | 4/2017 | Naerum et al. | |
| 2017/0283333 A1 | 10/2017 | Rosenthal et al. | |
| 2019/0010641 A1* | 1/2019 | Hjelmgaard | A01G 24/00 |
| 2019/0037792 A1 | 2/2019 | Leo et al. | |

FOREIGN PATENT DOCUMENTS

| | | |
|---|---|---|
| CN | 109452154 | 3/2019 |
| WO | 97/07664 | 3/1997 |
| WO | 2004/007615 | 1/2004 |
| WO | 2007/129202 | 11/2007 |
| WO | 2010/003677 | 1/2010 |
| WO | WO201208650 A1 * | 3/2012 |
| WO | 2014/122284 | 8/2014 |
| WO | 2016/061672 | 4/2016 |
| WO | 2017/114723 | 7/2017 |
| WO | 2017114724 | 7/2017 |

OTHER PUBLICATIONS

Alchimia Growing *Cannabis* in Rockwool 2016, retrieved on Dec. 1, 2020, retrieved from the Internet at https://www.alchimiaweb.com/blogen/grow-cannabis-rockwool/, 16 pp. (Year: 2016).*

Snoofer's illustrated rockwool cloning technique 2017, retrieved on Nov. 18, 2020, retrieved from the Internet at https://overgrow.eom/t/snoofers-illustrated-rockwool-cloning-technique/254, 8 pp. (Year: 2017).*

Whipker et al. Optimizing Electrical Conductivity (EC) in *Cannabis* Cultivation, *Cannabis* Business Times 2019, retrieved on Nov. 18, 2020, retrieved from the Internet at https://www.cannabisbusinesstimes.com/article/optimizing-electrcal-conductivity-ec/, 10 pp. (Year: 2019).*

International Search Report/Written Opinion, International Application No. PCT/EP2020/087981, dated Apr. 9, 2021, PCT/ISA/210, PCT/ISA/220, PCT/ISA/237, 10 pp.

How to Grow Marijuana on Rockwool—Greenman's Page, Feb. 13, 2019, http://www.greenmanspage.com/rockwool, 58 pp.

Growing *Cannabis* cuttings—Alchimia Grow Shop, May 28, 2015, http://www.alchimiaweb.com/blogen/growing-marijuana-cuttings/, 11 pp.

* cited by examiner

*Primary Examiner* — June Hwu
(74) *Attorney, Agent, or Firm* — Saliwanchik, Lloyd & Eisenschenk (57) ABSTRACT

Methods of propagating a *Cannabis* cutting are provided. A method of propagating a *Cannabis* cutting can include: providing a coherent growth substrate comprising man-made vitreous fibres bonded with a cured binder composition, the growth substrate having a density in the range of 60 kilograms per cubic meter ($kg/m^3$) to 70 $kg/m^3$; inserting the *Cannabis* cutting into the growth substrate at a location where the growth substrate does not have a seed hole; and providing a nutrient solution having an electrical conductivity value between 1.6 milli-Siemens per centimeter (mS/cm) and 2.4 mS/cm to the *Cannabis* cutting in the growth substrate.

20 Claims, 6 Drawing Sheets
(6 of 6 Drawing Sheet(s) Filed in Color)

METHOD OF PROPAGATING A *CANNABIS* CUTTING

FIELD OF THE INVENTION

The present invention is directed to a method of propagating *Cannabis* cuttings in a growth substrate comprising man-made vitreous fibres bonded with a cured binder composition.

BACKGROUND

*Cannabis* is a genus of flowering plants in the family Cannabaceae, with three recognised species: *Cannabis sativa; Cannabis* indica and *Cannabis ruderalis*. In recent years, *Cannabis* has been investigated and used for medicinal purposes. *Cannabis* contains cannabinoids which can be used medicinally, including tetrahydrocannabinol (THC) and cannabidiol (CBD). *Cannabis* has been used to treat, inter alia, nausea and vomiting (for example during chemotherapy), chronic pain and muscle spasms, and epilepsy.

It is known to grow *Cannabis* indoors and in large-scale greenhouses, in order to optimise growth conditions and obtain a good yield. U.S. Patent Application Publication No. US 2017/0283333 A1 discloses growing vegetables and medicinal plants, such as medical *Cannabis*, hydroponically.

*Cannabis* is an annual plant which completes its life cycle within one year or less and is dioecious, having both male and female plants. Medicinal *Cannabis* can be reproduced sexually or asexually. Seeds are the product of sexual propagation and cuttings (also called clones) are the results of asexual propagation. Cloning involves cutting a growing branch to obtain a "cutting'"; placing the cutting in a growing medium and allowing the cutting to grow and develop roots. Clones are taken from female plants with desirable medicinal qualities called mother plants. Essentially, cloning is taking one cell of a plant and promoting its growth into a plant: the new plant shares the same DNA and is a copy of the mother plant.

Asexual propagation (also called cloning) is particularly preferred for medicinal *Cannabis* for predictability and uniformity. In order to meet regulations for medicinal *Cannabis*, it is often necessary in jurisdictions to have very closely controlled growing conditions. For example, the final harvested product must be tested to ensure that no undesirable components are present (such as pesticides or bacteria) and that the required levels of cannabinoids are met.

Typically propagation is the first stage in growing medicinal *Cannabis*. Cuttings are taken and grown until a sufficient number of roots develop. The propagated cuttings are then moved to the next phase of growing, which is considered a separate growing process. During propagation, it is desirable to achieve the required number of cuttings with the highest success rate (i.e. the required root development for the nest stage). It is also desirable to have the propagated cuttings ready at the right moment. This ensures that the highest number of propagated cuttings proceed to the next growing stage together, and at the correct time.

Therefore, it would be desirable to maximise the number of healthy and viable propagated cuttings so that an increased percentage of cuttings develop roots and can be used in the next stage of growing. This would ultimately lead to a higher yield of final product (e.g. medicinal *Cannabis*).

In addition, it would be desirable to increase the uniformity of propagated cuttings, as this increases the quality of the end product (e.g., medicinal *Cannabis*).

Furthermore, it would be desirable to speed up the propagation process, as typically the slower the process, the lower the quality of the propagated cuttings. Therefore, it would be desirable to speed up propagation in order to achieve a high success rate of cuttings and more uniform cuttings.

International Patent Application No. WO 2016/061672 A1 discloses a method for optimising yield and accelerating growth of medicinal *Cannabis*. However, this method is complicated and expensive as it requires a growth chamber containing a climate controlled micro-climate under negative pressure.

Therefore, an aim of the present invention is to provide a method of propagating *Cannabis* cuttings which results in increased output by having a quicker propagation process, more uniform propagated cuttings and a higher number of propagated *Cannabis* cuttings that can proceed to the next growing stage. It is an aim of the invention to provide such a method that is efficient and economical.

BRIEF SUMMARY

In a first embodiment of the present invention, a method of propagating a *Cannabis* cutting can comprise the steps of:
  providing a coherent growth substrate comprising manmade vitreous fibres (MMVF) bonded with a cured binder composition, wherein the growth substrate has a density in the range of 60 kilograms per cubic meter ($kg/m^3$) to 70 $kg/m^3$;
  inserting the *Cannabis* cutting into the growth substrate at a location where the growth substrate does not have a seed hole; and
  providing a nutrient solution having an electrical conductivity (EC) value between 1.6 milli-Siemens per centimeter (mS/cm) and 2.4 mS/cm to the *Cannabis* cutting in the growth substrate.

In a second embodiment of the present invention, use of a coherent growth substrate for propagating a *Cannabis* cutting can comprise the steps of:
  inserting the *Cannabis* cutting into the growth substrate at a location where the growth substrate does not have a seed hole; and
  providing a nutrient solution having an electrical conductivity (EC) value between 1.6 and 2.4 mS/cm to the *Cannabis* cutting in the growth substrate;
  wherein the coherent growth substrate comprises manmade vitreous fibres (MMVF) bonded with a cured binder composition; and wherein the growth substrate has a density in the range of 60 $kg/m^3$ to 70 $kg/m^3$.

The present inventor has discovered that the methods of embodiments of the present invention increase the number of propagated cuttings that can proceed to the next stage of growing, resulting in a higher yield. Furthermore, the methods of embodiments of the present invention increase the uniformity of the cuttings, which ultimately leads to a more uniform and therefore higher quality end product. Uniformity and quality is of particular importance for medicinal *Cannabis* due to the high standards required for pharmaceutical products. In addition, the methods of embodiments of the present invention enable the step of propagation to be achieved in a shorter amount of time, which results in higher quality and uniformity of the end product. In particular, these benefits are achieved by having a growth substrate with a density in the range of 60-70 $kg/m^3$, and inserting the cutting into the substrate at a location that does not have a seed hole. In addition, this is achieved by providing the growth substrate and *Cannabis* cutting with a nutrient solution having an EC of 1.6 to 2.4 mS/cm.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DISCLOSURE

Embodiments of the present invention provide methods of propagating a *Cannabis* cutting, and in an embodiment a method can comprise the steps of:
providing a coherent growth substrate comprising man-made vitreous fibres (MMVF) bonded with a cured binder composition, wherein the growth substrate has a density in the range of 60 to 70 kg/m$^3$;
inserting the *Cannabis* cutting into the growth substrate at a location where the growth substrate does not have a seed hole; and
providing a nutrient solution having an electrical conductivity (EC) value between 1.6 and 2.4 mS/cm to the *Cannabis* cutting in the growth substrate.

In the present invention, the phrase "method of propagation" has its normal meaning in the field of plant growth substrates. Propagation is the first stage in growing *Cannabis*. Propagation is complete, and the cuttings are ready for the next stage of growing, when a root system has developed. In a root system, roots grow through the growth substrate and at least three roots have grown such that they protrude out of the side surfaces or bottom surface of the substrate. The term propagation is very well-understood in the art of growth substrates.

Figure 6:
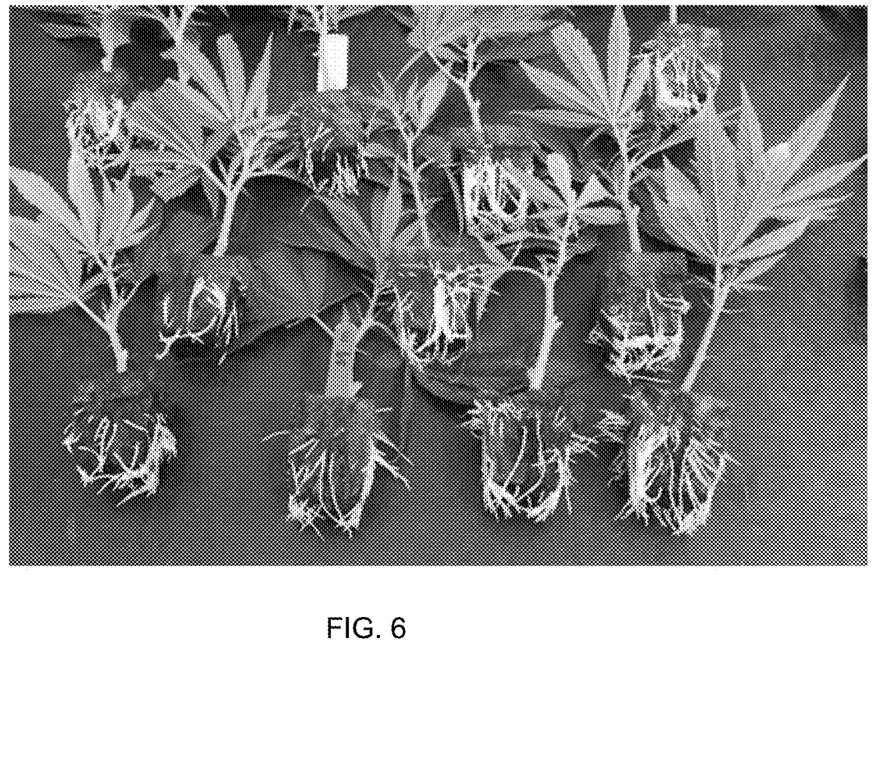
FIG. 6 shows a photograph of propagated *Cannabis* cuttings.

FIG. 6 shows a photograph of propagated *Cannabis* cuttings that are ready for the next stage of growing. All cuttings have developed a root system, with at least three roots protruding from the side or bottom surfaces of the growth substrate.

Typically, propagation lasts for 3 to 4 weeks. However, in embodiments of the present invention, propagation can last for 2 to 3 weeks, preferably 2 weeks or less. This has the significant advantage of leading to more uniform propagated cuttings, resulting in an end product with higher quality. In addition, speeding up the propagation process means that more cuttings can be produced in a year, thus increasing yield.

The term "*Cannabis*" refers to any plants from the Cannabaceae family such as *Cannabis sativa*, *Cannabis* indica and *Cannabis ruderalis*. *Cannabis* plants are also called marijuana or hemp. Preferably, embodiments of the present invention relate to medicinal *Cannabis*. By medicinal *Cannabis* it is meant *Cannabis* that meets the required regulations for being used to treat certain conditions.

In the present invention, the term "cutting" has its normal meaning in the art. It refers to a part of a plant that is cut from a growing branch or stem. A cutting, when initially cut from a plant, does not have any roots. Once propagated, a cutting will be a clone of the plant from which it was cut (called the mother plant).

Preferably, cuttings taken from the mother plant are between 10 to 14 days old; that is, the stem from which the cutting is taken developed between 10 to 14 days previous to the step of cutting. The mother plant may be older than 10 to 14 days. Preferably, the cuttings are 8 to 15 cm in length, more preferably 10 to 12 cm in length. Preferably the cuttings have a stem diameter of 3 to 8 millimeters (mm), most preferably 5 mm or about 5 mm (+1-5%). The inventors discovered that when the cuttings have the above length and/or diameter and/or age, this leads to fast development of the roots. Preferably all cuttings have the same height and age to maximise uniformity and quality of the end product.

In a preferred embodiment, the cutting is cut from the mother plant at an angle of 180° such that it could sit flat on a horizontal surface, preferably, after taking the cutting from the mother plant, lower and upper leaves are trimmed to minimize loss via evaporation.

Figure 5:
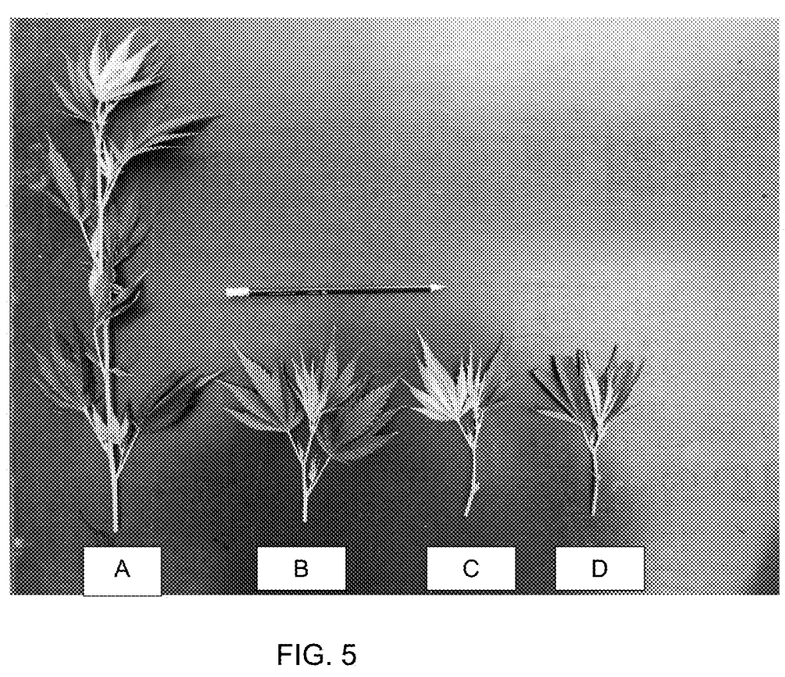
FIG. 5 shows a photograph of *Cannabis* cuttings.

FIG. 5 shows four cuttings from a *Cannabis* mother plant. Cutting A is a raw cutting taken from the mother plant. Cutting B is the shoot tip with a flat cut. Cutting C is a prepared cutting with any lower stems removed. Cutting D is a prepared cutting with larger leaves trimmed to restrict evaporation.

In embodiments of the present invention, a coherent growth substrate comprising man-made vitreous fibres (MMVF) is provided. The MMVF may be made by any of the methods known to those skilled in the art for production of MMVF growth substrate products. In general, a mineral charge is provided, which is melted in a furnace to form a mineral melt. The melt is then formed into fibres by means of rotational fiberisation. Preferably the coherent growth substrate is formed of man-made vireos fibres.

The melt may be formed into fibres by external centrifuging e.g. using a cascade spinner, to form a cloud of fibres. Alternatively, the melt may be formed into fibres by internal centrifugal fiberisation (e.g. using a spinning cup), to form a cloud of fibres.

Typically, these fibres are then collected to form a primary fleece or web, and the primary fleece or web is then cross-lapped to form a secondary fleece or web. The secondary fleece or web is then cured and formed into a growth substrate.

Binder and optionally wetting agent are usually added at the fiberisation stage by spraying into the cloud of forming fibres. These methods are well known in the art.

The MMVF can be of the conventional type used for formation of known MMVF growth substrates. It can be glass wool or slag wool but is usually stone wool. Stone wool generally has a content of iron oxide at least 3% and content of alkaline earth metals (calcium oxide and magnesium oxide) from 10 to 40%, along with the other usual oxide constituents of mineral wool. These may include silica, alumina, alkali metals (sodium oxide and potassium oxide), titania and other minor oxides. In general it can be any of the types of man-made vitreous fibre that are conventionally known for production of growth substrates.

The geometric mean fibre diameter is often in the range of 1.5 to 10 microns, in particular 2 to 8 microns, preferably 3 to 6 microns as conventional.

Preferably the growth substrate product comprises at least 90 wt % man-made vitreous fibres by weight of the total solid content of the growth substrate. An advantage of having such an amount of fibres present in the growth substrate product is that there are sufficient pores formed between the fibres to allow the growth substrate product to hold water and nutrients for the plant, whilst maintaining the ability for roots of the plants to permeate the growth substrate product. The remaining solid content may be made up primarily of binder and wetting agent.

The growth substrate product can be in the form of a coherent mass. That is, the growth substrate is generally a coherent matrix of man-made vitreous fibres, which has been produced as such, but can also be formed by granulating a slab of mineral wool and consolidating the granulated material. A coherent mass is a single unified substrate.

The growth substrate product comprises a cured binder composition, for example an organic binder, which is generally heat-curable. Preferably the growth substrate product comprises 1 to 10 wt % of binder based on the weight of the growth substrate product. More preferably, it comprises 2 to 6 wt %, most preferably 3 to 5 wt % binder.

The binder composition preferably comprises:
a) a sugar component; and
b) a reaction product of a polycarboxylic acid component and an alkanolamine component, wherein the binder composition prior to curing contains at least 42% by weight of the sugar component based on the total weight (dry matter) of the binder components. Such a binder composition may be used in embodiments of the present invention. This binder has the advantage of being formaldehyde-free and economical to produce.

The binder can be an organic hydrophobic binder, and in particular it can be a conventional heat-curable (thermosetting), binder of the type that has been used for many years in MMVF substrates (and other MMVF-based products). This has the advantage of convenience and economy. Thus, the binder is preferably a phenol formaldehyde resin or urea formaldehyde resin, in particular phenol urea formaldehyde (PUF) resin.

The binder may be a formaldehyde-free aqueous binder composition comprising: a binder component (A) obtainable (or obtained) by reacting at least one alkanolamine with at least one carboxylic anhydride and, optionally, treating the reaction product with a base; and a binder component (B) that comprises at least one carbohydrate (e.g., as disclosed in International Patent Application No. WO2004/007615, which is hereby incorporated by reference herein in its entirety). Binders of this type are hydrophilic.

International Patent Application No. WO97/07664, which is hereby incorporated by reference herein in its entirety, discloses a hydrophilic substrate that obtains its hydrophilic properties from the use of a furan resin as a binder. Binders of this type may be used in embodiments of the present invention.

International Patent Application No. WO07129202, which is hereby incorporated by reference herein in its entirety, discloses a hydrophilic curable aqueous composition wherein said curable aqueous composition is formed in a process comprising combining the following components:
(a) a hydroxy-containing polymer;
(b) a multi-functional crosslinking agent which is at least one selected from the group consisting of a polyacid, salt(s) thereof and an anhydride; and
(c) a hydrophilic modifier;

wherein the ratio of (a):(b) is from 95:5 (or about 95:5) to 35:65 (or about 35:65).

The hydrophilic modifier can be a sugar alcohol, monosaccharide, disaccharide or oligosaccharide. Examples given include glycerol, sorbitol, glucose, fructose, sucrose, maltose, lactose, glucose syrup and fructose syrup. Binders of this type can be used in the present invention.

The binder may be as described in International Patent Application No. WO 2017/114724, which is hereby incorporated by reference herein in its entirety, wherein the binder composition prior to curing comprises the following components:

a component (i) in the form of one or more compounds selected from
compounds of the formula, and any salts thereof:

in which R1 corresponds to H, alkyl, monohydroxyalkyl, dihydroxyalkyl, polyhydroxyalkyl, alkylene, alkoxy, amine;

compounds of the formula, and any salts thereof:

in which R2 corresponds to H, alkyl, monohydroxyalkyl, dihydroxyalkyl, polyhydroxyalkyl, alkylene, alkoxy, amine;

a component (ii) in the form of one or more compounds selected from the group of ammonia, amines or any salts thereof; and a component (iii) in the form of one or more carbohydrates.

The binder composition may be as described in International Patent Application No. WO 2017/114723, which is hereby incorporated by reference herein in its entirety, wherein the binder composition prior to curing comprises the following components:

a component (i) in form of one or more carbohydrates; and a component (ii) in form of one or more compounds selected from sulfamic acid, derivatives of sulfamic acid or any salt thereof.

The binder composition may be a composition comprising at least one hydrocolloid prior to curing. Preferably, the at least one hydrocolloid is selected from the group consisting of gelatin, pectin, starch, alginate, agar agar, carrageenan, gellan gum, guar gum, gum arabic, locust bean gum, xanthan gum, and cellulose derivatives such as carboxymethylcellulose, arabinoxylan, cellulose, curdlan, and β-glucan.

The growth substrate product can optionally include a wetting agent. This increases the amount of water that the growth substrate product can absorb. The use of a wetting agent in combination with a hydrophobic binder results in a hydrophilic growth substrate product. Therefore, preferably when the binder is hydrophobic, the growth substrate product comprises a wetting agent.

The binder can be hydrophilic. A hydrophilic binder does not require the use of as much wetting agent as a hydrophobic binder. However, a wetting agent in embodiments of the subject invention can be used to increase the hydrophilicity of a hydrophilic binder in a similar manner to its action in combination with a hydrophobic binder. This means that the MMVF substrate will absorb a higher volume of water than if the wetting agent is not present.

The wetting agent can be cationic, anionic or non-ionic. The growth substrate product may comprise a non-ionic wetting agent such as Rewopal®.

Preferably, the growth substrate product comprises an ionic surfactant, more preferably an alkyl ether sulphate surfactant wetting agent. The wetting agent may be an alkali metal alkyl ether sulphate or an ammonium alkyl ether sulphate. Preferably the wetting agent is a sodium alkyl ether sulphate. A commercially available alkyl ether sulphate surfactant wetting agent is Texapon®. The wetting agent may also be a linear alkyl benzene sulphonate anionic surfactant. These preferred wetting agents have been found to offer beneficial effects, particularly improving the hydrophilicity of the binder system.

Some non-ionic wetting agents may be washed out of the MMVF substrate over time. It is therefore preferable to use an ionic wetting agent, especially an anionic wetting agent, such as linear alkyl benzene sulphonate or Texapon®. These do not wash out of the MMVF substrate to the same extent.

Preferably the growth substrate product comprises 0.01 to 1 wt % wetting agent, preferably 0.05 to 0.5 wt % wetting agent, more preferably 0.1 to 0.3 wt % wetting agent.

The hydrophilicity of a sample of MMVF substrate can be measured by determining the sinking time of a sample. A sample of MMVF substrate having dimensions of 100×100×65 mm can be used (or even required in some cases) for determining the sinking time. A container with a minimum size of 200×200×200 mm is filled with water. The sinking time is the time from when the sample first contacts the water surface to the time when the test specimen is completely submerged. The sample is placed in contact with the water in such a way that a cross-section of 100×100 mm first touches the water. The sample will then need to sink a distance of just over 65 mm in order to be completely submerged. The faster the sample sinks, the more hydrophilic the sample is. The MMVF substrate is considered hydrophilic if the sinking time is less than 120 seconds. Preferably the sinking time is less than 60 seconds. In practice, the MMVF substrate may have a sinking time of a few seconds, such as less than 10 seconds.

The growth substrate product preferably has a volume in the range 3 to 300 $cm^3$.

The growth substrate product may have dimensions conventional for the product type commonly known as a plug. Preferably, the growth substrate product is a cube. Preferably the growth substrate product has a height of 30 to 50 mm, a width of 30 to 50 mm and a depth of 25 to 45 mm, Alternatively the growth substrate may be of the type of plug described as the first coherent MMVF growth substrate in International Patent Application No. WO2010/003677, which is hereby incorporated by reference herein in its entirety. In this case the volume of the growth substrate product is most preferably in the range to 10 to 40 $cm^3$.

In another embodiment, the growth substrate product is preferably a cube with dimensions of 4 cm by 4 cm by 4 cm. Preferably, this product has a liquid-impermeable plastic covering surrounding its side surfaces only (i.e., the bottom and top surfaces are not covered).

In an alternative embodiment, the growth substrate product is preferably cylindrical. Preferably it has a length of 50 mm and a diameter of 46 mm, or a length of 40 mm and a diameter of 36 mm, or a length of 27 mm and a diameter of 22 mm.

In the present invention, the term "height" means the distance from the bottom surface to the top surface when the substrate is in use. The top surface is the surface that faces upwardly when the product is positioned as intended to be used and the bottom surface is the surface that faces downwardly (and on which the product rests) when the product is positioned as intended to be used. The term "length" means the longest distance between two sides i.e. the distance from one end to the other end when the substrate is in use. The term "width" is the distance between two sides, perpendicular to the length. These terms have their normal meaning in the art.

In the methods according to embodiments of the present invention, the growth substrate product has a density in the range of 60 kg/m3 to 70 $kg/m^3$. The inventors surprisingly discovered that when the density is in this range, there is an improved root development of the cuttings and the number of cuttings that can progress to the next growing stage is improved. In addition, the present inventors discovered that when the density of the growth substrate product is in this range, it is possible to insert the *Cannabis* cutting into the substrate directly. This removes the requirement for having a seed hole, which leads to significant advantages as discussed below.

In a preferred embodiment, the density of the growth substrate is 65 $kg/m^3$ (or about 65 $kg/m^3$ (+/−5%)).

In the methods of embodiments of the present invention, the *Cannabis* cutting is inserted into the growth substrate at a location where the growth substrate does not have a seed hole. By this, it is meant that the cutting is not inserted into a seed hole. It is not excluded that the growth substrate has a seed hole at a different location from where the cutting is inserted. However, preferably the growth substrate does not comprise a seed hole.

The term seed hole has its normal meaning in the art, and can also be called a plant hole or cavity. A seed hole is an indentation in the top surface of a growth substrate, into which a seed or cutting is placed. By stating that the growth substrate is inserted into a location that does not have a seed hole it is meant that it is inserted into a location of the growth substrate that does not have any significant indentations (i.e., does not have any indentations with a depth of greater than 3 mm, more preferably greater than 1 mm, most preferably greater than 0.5 mm).

The inventor surprisingly discovered that when the *Cannabis* cutting is inserted into a location of the growth substrate that not have a seed hole, there is an improvement in root development and the number of cuttings that can progress to the next growing stage is improved. Due to the density of the growth substrate of the invention, the cutting can be inserted directly in the growth substrate and is able to develop roots optimally. Without being bound by theory, it is believed that the cutting is held in the growth substrate in a more optimal way, thus allowing more optimal growth conditions.

The methods of embodiments of the present invention comprise the step of inserting the *Cannabis* cutting into the growth substrate. Due to the porous nature of the MMVF growth substrate, and the density of 60 to 70 kg/m³, the *Cannabis* cutting can be inserted by simply pushing the cut end of the cutting into the top surface. This can be done manually by hand or by use of automation equipment. Preferably, the cutting is inserted between 5 to 10 mm into the top surface of the growth substrate. Preferably, the cutting is inserted into the centre of the top surface. This ensures that the cutting can develop roots with maximum length in all directions. It therefore makes full use of the growth substrate volume.

In a preferred embodiment, prior to inserting the cutting into the growth substrate product, the cut end of the cutting is dipped into a rooting hormone, for example, an indole-3-butyric acid root hormone.

In the methods of embodiments of the present invention, the *Cannabis* cutting in the growth substrate is provided with a nutrient solution having an electrical conductivity (EC) value between 1.6 and 2.4 mS/cm. Preferably, the nutrient solution has an EC value of 1.8 to 2.2 mS/cm, most preferably 2.0 mS/cm (or about 2.0 mS/cm (=/−5%)).

The EC value can be measured in accordance with ISO 7888 1985. The EC (electrical conductivity) is measured by determining the resistance of a solution (nutrients and water in the substrate) between two or more electrodes separated by a fixed distance. The EC can be measured using the water content meter described in International Patent Application No. WO2014122284, which is hereby incorporated by reference herein in its entirety.

Preferably the nutrient solution is supplied using an ebb flood system. This is well-known to the skilled person. For example, the growth substrate is placed on a bench or the floor and flooded with nutrient solution and left for 5 to 15 minutes, before draining. An ebb flood system works by temporarily making the cultivation tables "too full" (i.e. with an excess) of nutrient solution during a pre-calculated amount of time and then letting the solution flow back to the reservoir. The refluxed nutrient solution is checked and re-enriched with nutrients, after which it is reused by periodically pumping it back to the cultivation tables.

Preferably the growth substrate product is firstly saturated with water and nutrient solution having an EC value between 1.6 and 2.4 mS/cm. By saturated it is meant that the growth substrate product has a water content value of close to 100% (i.e., 95 to 100%); that is, the growth substrate holds the maximum amount of water possible. This may be done by immersing the growth substrate in a nutrient bath, wherein the nutrient solution has an EC value between 1.6 and 2.4 mS/cm. Preferably the growth substrate is immersed for 5 to 15 minutes. Alternatively, the growth substrate may be saturated by using an ebb flood bench or floor.

The growth substrate product can be saturated before or after the cutting is inserted. Preferably the growth substrate product is saturated before the cutting is inserted.

After the preferred initial saturation, the growth substrate is irrigated to maintain a water content value in the range of 30 to 80% (expressed as a percentage of the total amount of water required to saturate the substrate).

It is desirable to wait for as long as possible to water the cuttings, so the roots develop in search for nutrients and water. It is undesirable to maintain a water content value of close to 100% in the substrate, to ensure the required amount of oxygen is achieved. This makes sure the roots are not drowned and do not develop root rot leading to plant necrosis.

Preferably the nutrient solution having an electrical conductivity (EC) value between 1.6 and 2.4 mS/cm is provided to the growth substrate product containing the *Cannabis* cutting every 2 to 10 days. In the winter it is possible to wait until day 12 before watering once at the end of the propagation period. In summer, when temperatures are high and the radiation of the sun is high, water is preferably given more than once.

Preferably, during the methods of embodiments of the present invention, the substrate is irrigated only three times or twice or once.

The growth substrate may comprise further additives, such as a controlled-release fertiliser.

In an embodiment of the present invention, use of a coherent growth substrate for propagating a *Cannabis* cutting, can comprise the steps of:
  inserting the *Cannabis* cutting into the growth substrate at a location where the growth substrate does not have a seed hole; and
  providing a nutrient solution having an electrical conductivity (EC) value between 1.6 and 2.4 mS/cm to the *Cannabis* cutting in the growth substrate;
  wherein the coherent growth substrate comprises man-made vitreous fibres (MMVF) bonded with a cured binder composition; and wherein the growth substrate has a density in the range of 60 kg/m³ to 70 kg/m³. This embodiment of the invention may have any of the additional features described above for the method of the invention.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1

A comparative experiment was designed to identify the effect of inserting the *Cannabis* cutting into a location where the growth substrate does not have a seed hole.

MMVF growth substrates having a density of 65 kg/m³ were compared with and without seed/plant holes.

Two strains of *Cannabis* were investigated—Powerplant and Afghani.

First, cuttings were made from the same mother plant for each strain. The cuttings were then inserted into the growth substrates. For the growth substrates with a seed/plant hole, the cuttings were inserted into the hole. For growth substrates without a seed/plant hole, the cuttings were inserted into the top face of the substrate.

The cuttings were supplied with a feed solution having an EC value of 2.4 mS/cm and a pH of 5.5.

The growth substrates were analysed after 13 days, and categorised according to the following three options:
  No roots visible=no roots
  1 to 3 visible roots=root tips
  3 or more roots=ready
  Stage 1 (after 13 days)

| Number of Substrates | Strain | Design | Ready | Root tips | No roots |
|---|---|---|---|---|---|
| 40 | Powerplant | No plant hole | 17 (42.5%) | 8 (20%) | 15 (37.5%) |
| 40 | Powerplant | Plant hole | 5 (12.5%) | 7 (17.5%) | 28 (70%) |
| 40 | Afghani | No plant hole | 24 (60%) | 6 (15%) | 10 (25%) |
| 40 | Afghani | Plant hole | 20 (50%) | 7 (17.5%) | 13 (32.5%) |

After 13 days, it can be seen that for both strains of *Cannabis*, the percentage of cuttings which were ready for the next stage was significantly higher for substrates without seed/plant holes. Equally, the number of cuttings which did not develop any roots was significantly higher for growth substrates with seed/plant holes. Therefore, the data show that the effect of not having a seed/plant hole is an improvement in root development and the number of cuttings that can progress to the next growing stage.

Example 2

An experiment was designed to investigate the effect of having a density in the range of 60-70 kg/m$^3$.

MMVF growth substrates with a density of 65 kg/m$^3$ ("GC65") were compared with MMVF growth substrates having a density of 75 kg/m$^3$ ("GC75").

Figure 1A:
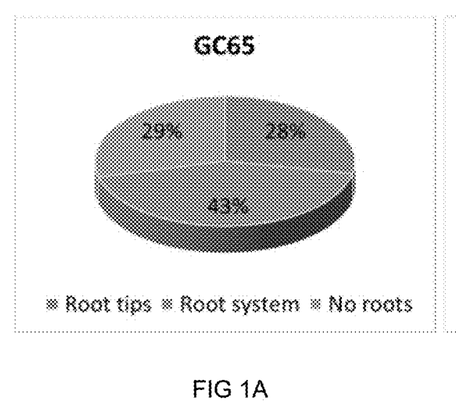
FIGS. 1A to 1D show the results of an experiment on growth substrates with varying densities. In each of FIGS. 1A to 1D, the bottom slice of the pie chart is for root system, the top-left slice of the pie chart is for no roots, and the top-right slice of the pie chart is for root tips.
Figure 1B:
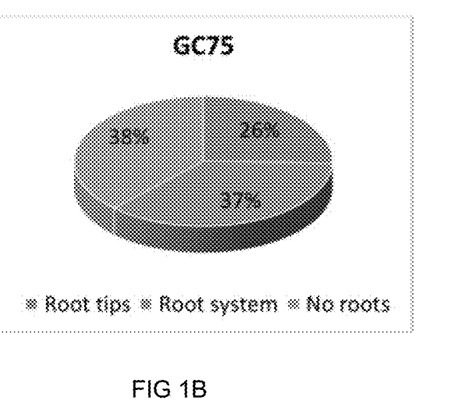
Figure 1C:
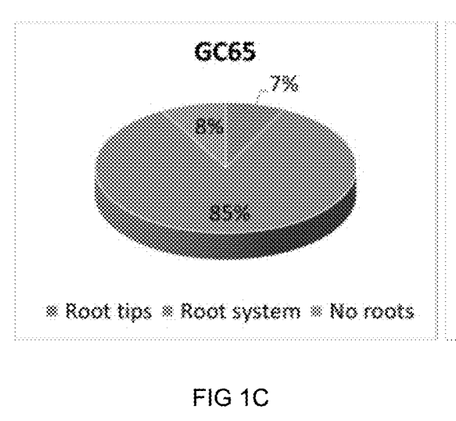
Figure 1D:
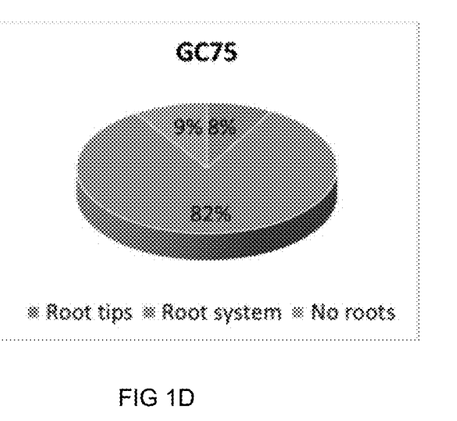

The results are shown in FIGS. 1A to 1D. FIGS. 1A and 1B show the results after 10 days, and FIGS. 1C and 1D show results after 14 days. The growth substrates were categorised after 10 and 14 days according to the following:
No roots visible=no roots
1 to 3 visible roots=root tips
3 or more roots=root system The growth substrates according to the invention, with a density of 65 kg/m$^3$, had a higher percentage of cuttings with root systems and roots tips after 10 days. The same was true after 14 days.

Therefore, the data show that the effect of a density in the range of 60-70 kg/m$^3$ is an improvement in root development and the number of cuttings that can progress to the next growing stage.

Example 3

An experiment was carried out to investigate the effect of different nutrient solutions. Three solutions were tested: EC=1.5; EC=2.0; EC=2.5 mS/cm.

Cuttings were inserted into growth substrates having a density of 65 kg/m3. The cuttings were first dipped in root hormone (Clonex® IBA gel 0.3%) and then inserted into the substrates. The substrates were irrigated on days 2, 4, 6, 8, 10 and 12 with different solutions (EC 1.5, 2.0, 2.5 mS/cm) and supplied with artificial light for 18 hours a day.

Figure 2A:
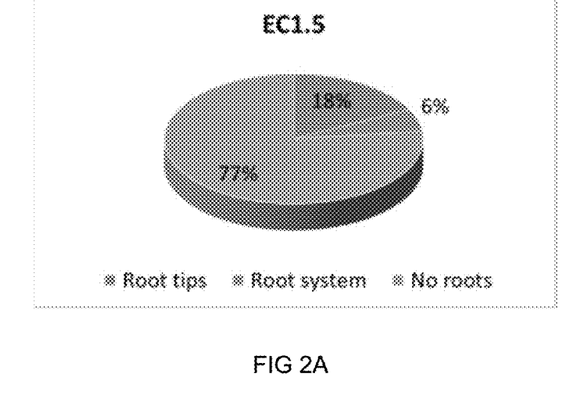
FIGS. 2A to 2C show the results of an experiment on growth substrates with different nutrient solutions after 10 days. In each of FIGS. 2A to 2C, the bottom/left slice of the pie chart is for no roots, the top-right slice of the pie chart is for root tips, and the right/bottom-right slice of the pie chart is for root system.
Figure 2B:
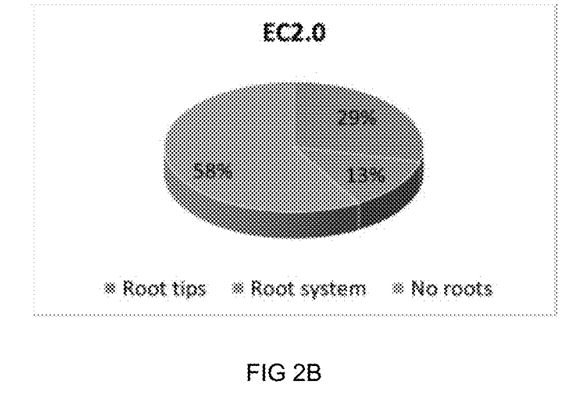
Figure 2C:
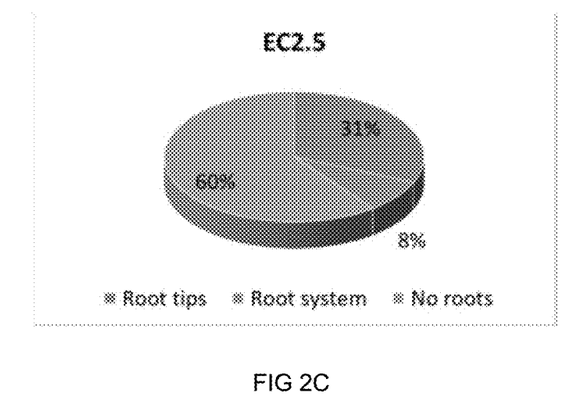
Figure 3A:
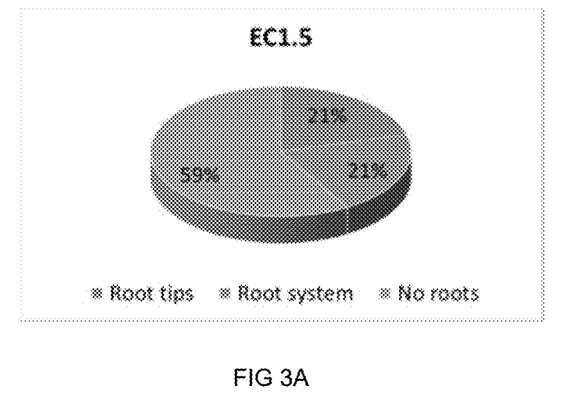
FIGS. 3A to 3C show the results of an experiment on growth substrates with different nutrient solutions after 12 days. In each of FIGS. 3A to 3C, the top-left slice of the pie chart is for no roots, the top-right slice of the pie chart is for root tips, and the bottom-right slice of the pie chart is for root system.
Figure 3B:
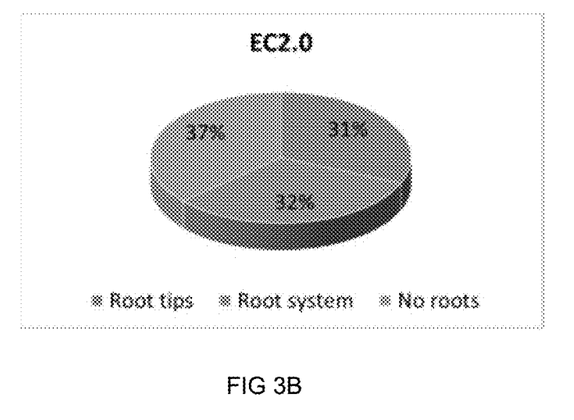
Figure 3C:
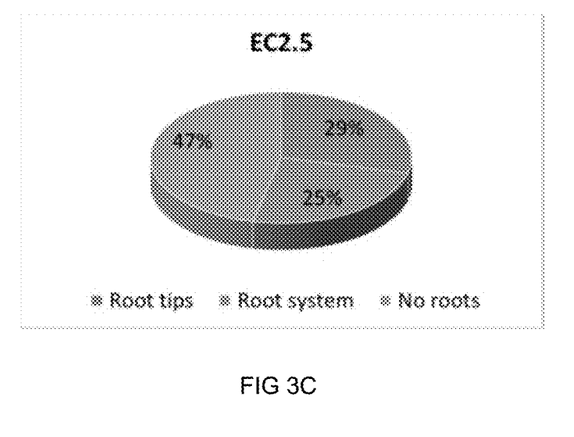
Figure 4A:
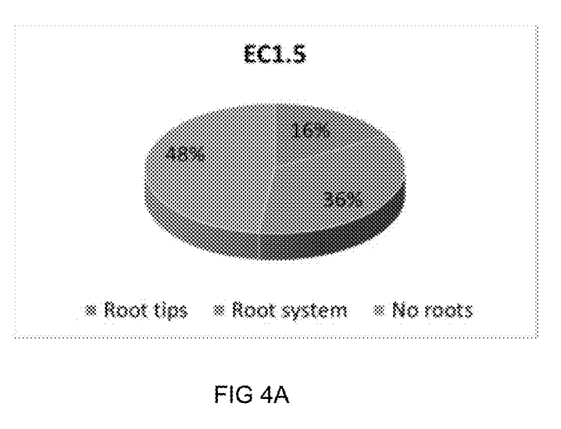
FIGS. 4A to 4C show the results of an experiment on growth substrates with different nutrient solutions after 14 days. In each of FIGS. 4A to 4C, the top-left slice of the pie chart is for no roots, the top-right slice of the pie chart is for root tips, and the bottom/bottom-right slice of the pie chart is for root system.
Figure 4B:
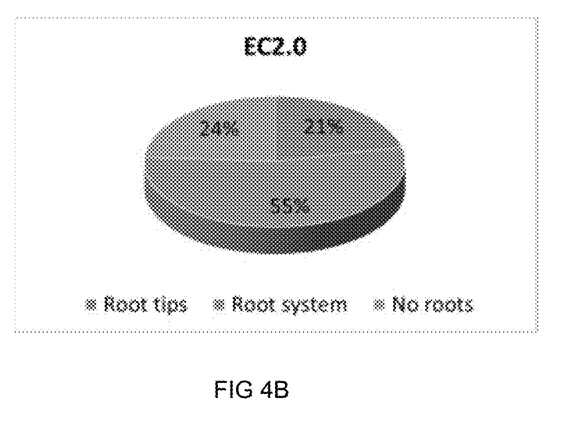
Figure 4C:
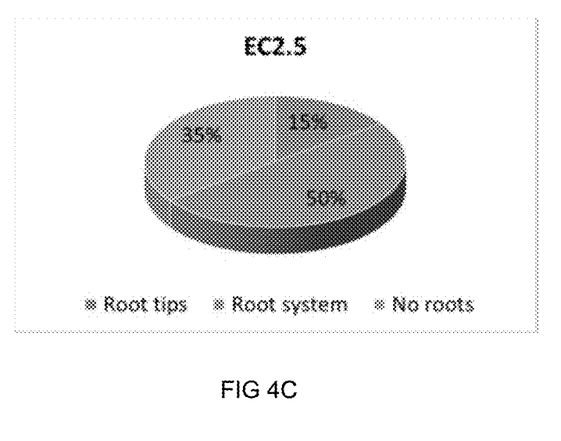

The substrates were analysed after 10 days, 12 days and 14 days and the results shown in FIGS. 2-4. FIGS. 2A-C shows the results after 10 days; FIGS. 3A-C show the results after 12 days; and FIGS. 4A-C show the results after 14 days.

The growth substrates were categorised after 10, 12 and 14 days according to the following:
No roots visible=no roots
1 to 3 visible roots=root tips
3 or more roots=root system From the results in FIGS. 2-4, it can be seen that the growth substrates supplied a nutrient solution of EC=2.0 mS/cm had the highest percentage of roots systems and root tips after each stage.

Therefore, the data show that the effect of an EC value 1.6 to 2.4 mS/cm is an improvement in root development and the number of cuttings that can progress to the next growing stage.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A method of propagating a *Cannabis* cutting, the method comprising the steps of:
   i) providing a coherent growth substrate comprising man-made vitreous fibres (MMVF) bonded with a cured binder composition, wherein the coherent growth substrate has a density in a range of 60 kg/m$^3$ to 70 kg/m$^3$;
   ii) inserting the *Cannabis* cutting into the coherent growth substrate at a location where the coherent growth substrate does not have a seed hole; and
   iii) providing a nutrient solution having an electrical conductivity (EC) value between 1.6 mS/cm and 2.4 mS/cm to the *Cannabis* cutting in the coherent growth substrate.

2. The method according to claim 1, wherein the binder composition comprises:
   a) a sugar component; and
   b) a reaction product of a polycarboxylic acid component and an alkanolamine component,
   wherein the binder composition prior to curing contains at least 42% by weight of the sugar component based on the total dry matter weight of binder components of the binder composition.

3. The method according to claim 1, wherein the method lasts 2 to 3 weeks.

4. The method according to claim 1, wherein the method lasts less than 2 weeks.

5. The method according to claim 1, wherein the *Cannabis* cutting inserted into the coherent growth substrate is 10 to 14 days old when cut from a mother plant.

6. The method according to claim 1, wherein the *Cannabis* cutting inserted into the coherent growth substrate has a length in a range of 8 to 15 cm.

7. The method according to claim 1 wherein the *Cannabis* cutting inserted into the coherent growth substrate has a stem diameter in a range of 3 to 8 mm.

8. The method according to claim 1 wherein the *Cannabis* cutting inserted into the coherent growth substrate has a length in a range of 10 to 12 cm and a stem diameter of 5 mm.

9. The method according to claim 1, wherein the *Cannabis* cutting is inserted into the coherent growth substrate such that the cutting is 5 to 10 mm below a top surface of the coherent growth substrate.

10. The method according to claim 1, wherein the coherent growth substrate has a cube shape.

11. The method according to claim 1, wherein the coherent growth substrate has a density of 65 kg/m$^3$.

12. The method according to claim 1, wherein step iii is performed twice.

13. The method according to claim 1, further comprising an additional step of saturating the coherent growth substrate with nutrient solution having an EC value between 1.6 and 2.4 mS/cm.

14. The method according to claim 13, wherein this additional step of saturating the coherent growth substrate is performed prior to inserting the *Cannabis* cutting into the coherent growth substrate.

15. The method according to claim 13, wherein a water content of the coherent growth substrate is maintained between 30 to 80% after the additional step of saturating the coherent growth substrate.

16. The method according to claim 1, wherein the coherent growth substrate comprises an alkyl ether sulphate surfactant wetting agent.

17. The method according to claim 1, wherein the entire coherent growth substrate does not comprise any seed holes.

18. Use of a coherent growth substrate for propagating a *Cannabis* cutting, the use comprising the steps of:
   i) inserting the *Cannabis* cutting into the coherent growth substrate at a location where the coherent growth substrate does not have a seed hole; and
   ii) providing a nutrient solution having an electrical conductivity (EC) value between 1.6 mS/cm and 2.4 mS/cm to the *Cannabis* cutting in the coherent growth substrate;
   wherein the coherent growth substrate comprises man-made vitreous fibres (MMVF) bonded with a cured binder composition; and
   wherein the coherent growth substrate has a density in a range of 60 kg/m$^3$ to 70 kg/m$^3$.

19. The use according to claim 18, wherein the binder composition comprises:
   a) a sugar component; and
   b) a reaction product of a polycarboxylic acid component and an alkanolamine component,
   wherein the binder composition prior to curing contains at least 42% by weight of the sugar component based on the total dry matter weight of binder components of the binder composition.

20. The use according to claim 18, wherein the *Cannabis* cutting inserted into the coherent growth substrate is 10 to 14 days old when cut from a mother plant,
   wherein the *Cannabis* cutting inserted into the coherent growth substrate has a length in a range of 8 to 15 cm,
   wherein the *Cannabis* cutting inserted into the coherent growth substrate has a stem diameter in a range of 3 to 8 mm,
   wherein the *Cannabis* cutting is inserted into the coherent growth substrate such that the cutting is 5 to 10 mm below a top surface of the coherent growth substrate, and
   wherein the coherent growth substrate comprises an alkyl ether sulphate surfactant wetting agent.

* * * * *